United States Patent [19]

Forsythe, Jr. et al.

[11] 4,214,993
[45] Jul. 29, 1980

[54] APPARATUS FOR SEPARATING FLUIDS

[75] Inventors: Jesse G. Forsythe, Jr., Media, Pa.; Donald R. Johnson, Wilmington; Linda M. St. Onge, Newark, both of Del.

[73] Assignee: E. I. Du Pont de Nemours and Company, Wilmington, Del.

[21] Appl. No.: 892,507

[22] Filed: Apr. 3, 1978

[51] Int. Cl.² ............................................. B01D 27/02
[52] U.S. Cl. .................................. 210/282; 210/455; 422/101
[58] Field of Search .................. 23/259, 292; 206/514, 206/519, 520; 210/248, 261, 282, 337, 338, 339, 361, 362, 446, 451, 455, 474, 476–478, 266, 283; 222/189; 422/101

[56] References Cited

U.S. PATENT DOCUMENTS

| 2,808,154 | 10/1957 | Scott | 210/476 |
|---|---|---|---|
| 3,492,396 | 1/1970 | Dalton et al. | 424/12 |
| 3,567,029 | 3/1971 | Quame | 210/282 |
| 3,721,528 | 3/1973 | Mead et al. | 23/259 |
| 3,768,979 | 10/1973 | Mead et al. | 23/259 |
| 3,800,947 | 4/1974 | Smith | 210/117 |
| 3,807,955 | 4/1974 | Note et al. | 206/514 |
| 3,810,545 | 5/1974 | Filz et al. | 210/198 C |
| 4,039,435 | 8/1977 | Narva | 206/519 |
| 4,151,254 | 4/1979 | Gimovsky | 210/282 |

FOREIGN PATENT DOCUMENTS 2314756  1/1977  France .

OTHER PUBLICATIONS

"Amber-Hi-Lites", Rohm and Haas Company, Technical Bulletin, No. 141, Jul. 1974.

Primary Examiner—Ivars C. Cintins

[57] ABSTRACT

An apparatus for separating fluids is formed essentially of three pieces which may be nested together to form a stacked array. The three pieces are a cap, an extraction cartridge housing a separating column, and a primary recovery cup. A secondary recovery cup may also be nested onto the lower end of the waste cup. The primary recovery cup has interior flanges for positioning and protecting the bottom end of the column against damage. Each of the elements has an enlarged upper portion forming an exterior step which facilitates mounting in the swinging bucket of a centrifuge. The column itself may comprise particles of a suitable separatory material with the top and the bottom of the particles retained by porous supports.

12 Claims, 3 Drawing Figures

U.S. Patent    Jul. 29, 1980    4,214,993
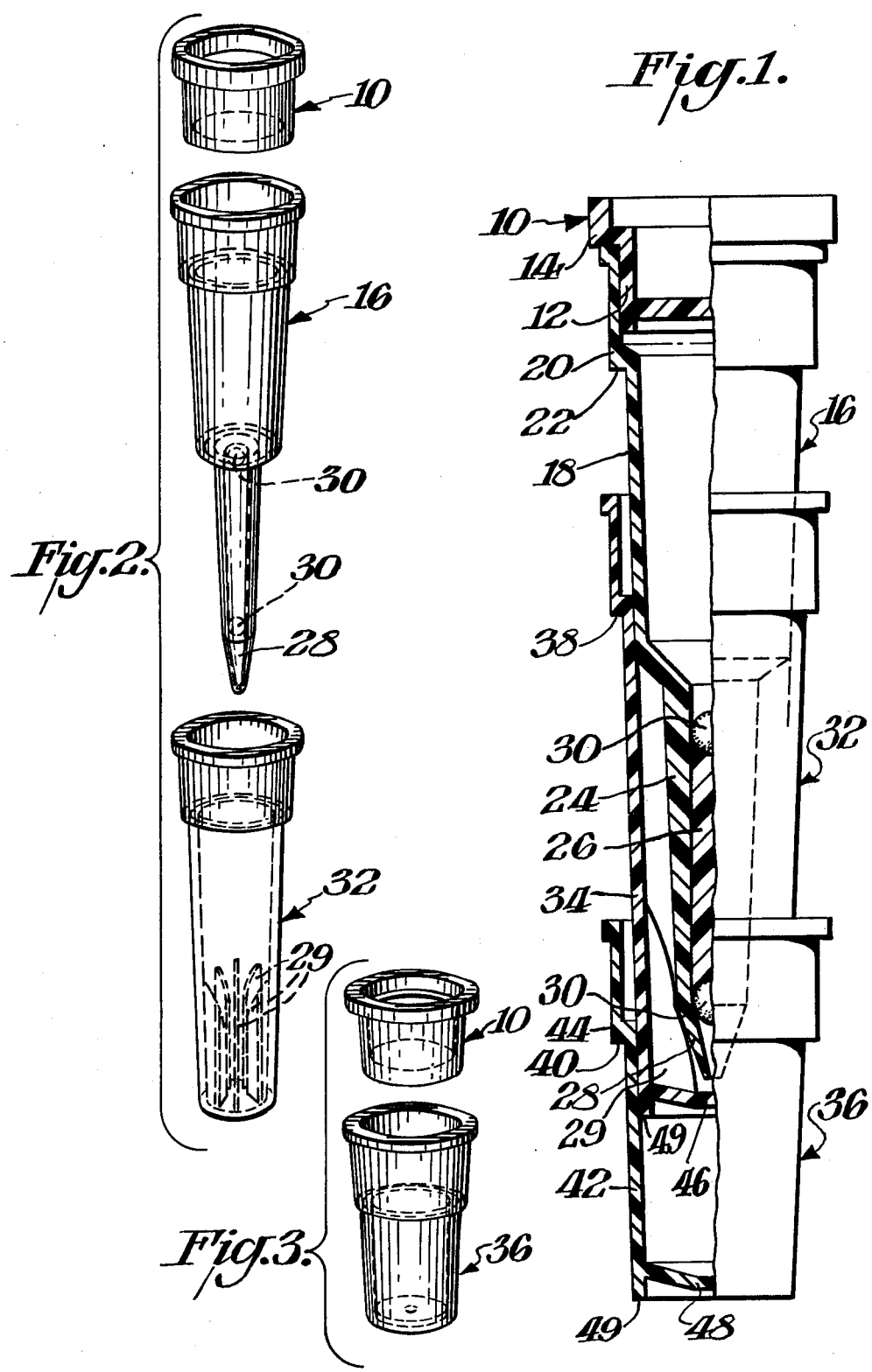

APPARATUS FOR SEPARATING FLUIDS

DESCRIPTION

1. Technical Field

This invention relates to apparatus separating components in fluids.

2. Background Art

It is often necessary in the analysis of samples, particularly biological samples, i.e., physiological fluids such as whole blood, serum or urine, to separate or extract the desired components for the sample.

One such extraction technique is described by Quame in U.S. Pat. No. 3,567,029. Quame describes the use of a disposable separating column filled with a particular solid phase, capable of extracting certain lipophilic compounds, including the most commonly encountered, abused drugs, such as phenobarbital, amphetamine, methadone and the like. In a typical drug extraction, such as from a urine sample, Quame allows the urine sample to pass through the column. The column selectively adsorbs any lipophilic drugs contained in the urine, thereby extracting the lipophilic drugs from the aqueous phase. Next, the adsorbed drugs are eluted from the column by a solvent and any residual aqueous phase is retained by a filter.

Unfortunately, however, this technique is somewhat time consuming because it is manual and because the sample and solvent phases slowly pass through the column and filter combination.

Further, the Quame column is relatively expensive to construct, requiring numerous pieces to form and assemble. Also, the Quame column cannot easily be used in a centrifuge even if it is desired to speed up its operation.

It is therefore an object of this invention to provide an improved apparatus for processing fluids.

SUMMARY OF THE INVENTION

According to one aspect of the invention, an apparatus for separating fluids includes an extraction cartridge, having an enlarged middle portion, tapered inward toward its lower end and adapted to receive said fluids and a tubular lower portion communicating with the upper portion, separating column material disposed in the lower portion, the bottom end of the lower portion defining a nozzle for fluids passing through the lower portion, a primary container, the interior lower end of the container defining interiorly extending radial guides for positioning the lower portion of the extraction cartridge and protecting the nozzle, the top end of each of the extraction cartridge and the primary container defining enlarged sections of equal inside diameter, a closure member insertable into the top end of either the extraction cartridge or the primary container, the extraction cartridge middle portion and the primary container each formed to have a mating taper to permit the nesting of the cartridge in the container, whereby the container and the closure member protect and seal the separating column material and the nozzle against loss of liquid and damage.

A secondary container may also be included and is formed to have a mating taper with the primary container to permit the nesting of the primary container in the secondary container. This facilitates a unit in which the column material is completely sealed for shipment to prevent its drying out and yet the primary and secondary containers may be easily separated in use to be placed in the appropriate swinging bucket of a centrifuge, for example.

BRIEF DESCRIPTION OF THE DRAWINGS

FIG. 1 is an elevation view of a nested separating apparatus, partially cut away to depict its shipping condition, constructed in accordance with this invention;

FIG. 2 is an exploded view showing the structure of three of the elements of the nested apparatus, namely, the cap, the extraction cartridge and the primary cup; and FIG. 3 is an exploded view of the secondary cup and cap which may be utilized, once a sample is separated for recovery of the desired components.

DETAILED DESCRIPTION OF THE INVENTION

The apparatus of this invention may find use in a swinging bucket centrifuge capable of switching between different fluid flow paths as is described in a copending application of Forsythe et al., entitled Centrifugal Method and Apparatus for Processing Fluid Materials. The ability to effect fluid switching while centrifuging the flow paths has many applications. One application is the extraction of a desired component from a physiological fluid sample. In this application, an extraction cartridge 32 containing a separating column with a resin bed (FIGS. 1 and 2) is separated from the nested stack, as will be described, and placed in a centrifuge rotor, in an orientation so that fluids are moved through the column by centrifugal force. The extraction cartridge is positioned radially inside of a circumferentially positioned first container or cup 32 and a second container or cup 36. The centrifuge rotor that will be described has a capability of switching the fluid flow path from the exit of the separating column in the extraction cartridge such that the effluent from the extraction cartridge may be passed by choice either to the first cup 32 or to the second cup 36.

The rotor used is a swinging bucket rotor capable of holding a plurality of sets of extraction cartridges, first cup, and second cups. For simplicity, the description will be in terms of a single set. Hence, as the rotor turns, say in a first sense, such as clockwise, the tip of the separating column is radially aligned with the first cup. The centrifugal force acting on the horizontal (radially disposed) column forces the sample through the resin bed at a controlled flow rate. The materials to be extracted from the sample are retained by the resin while other materials pass through the column and are collected in the first cup. Next, a predetermined volume of wash solvent or reagent is delivered to the fluid distribution hub of the rotor. The wash is divided into equal aliquots and directed to the resin beds in each separating column and collected in each first cup.

In this step the wash removes unadsorbed sample components from the resin bed. In the next step, rotational speed is increased so that the resulting increased centrifugal force passes residual wash to the first cup. The direction of rotor rotation is changed to shift the tip of the separating column in the extraction cartridge into radial alignment with the second cup. Eluting solvent is dispensed from a solvent reservoir and aliquoted to the several cartridge positions. The solvent passes through the column of the extraction cartridge under the influence of centrifugal force, extracting the adsorbed materials which are eluted from the resin bed of the column and collecting them in the second cup. The rotor is now slowed, and jets of (heated) air are directed to the second cup from an annular ring appropriately located. The eluted solvent is evaporated, leaving a dry residue of the extracted materials in the second cup.

The extraction cartridge 16 and the containers or caps 32 and 36 used in this technique are adapted to be nested together as seen in FIGS. 1 and 2 with a cap 10. Together they comprise a unit suitable for shipping and storage that may find various separatory uses similar to that described above. The cap 10, may be molded, as are all the parts, of a suitable inert material that will not interfere with the proposed test. Plastics that may be used are low or high density polyethylene, polypropylene, and like materials. The cap 10 is in the general configuration of a plug or stem portion 12 having an upper englarged step portion forming a flange 14 which aids in its removal from the extraction cartridge 16.

The extraction cartridge 16 is comprised essentially of three sections, a middle portion 18 which is adapted to hold a fluid, an upper portion 20 which has an enlarged internal diameter to accommodate the stem portion 12 of the cap 10 and which forms an exterior step shoulder 22 which facilitates positioning the extracting cartridge in a holder, such as the swinging bucket of a centrifuge. Finally there is a lower portion 24 which is a greatly reduced diameter and forms a constant diameter interior tube or column in which there may be disposed a separating material 26. The bottom tip end is in the form of a nozzle 28 which is tapered to a general point. Spherical porous supports 30 (frits), made of a typical inert plastic such as polyethylene, are placed at the top and bottom of the particular separating material 26 formed in the column to maintain the particles in place. The middle portion 18 is tapered inwardly towards the lower end to accommodate its being nested or stacked into the third element making up the nested separating apparatus of this invention, namely, the first cup 32.

The first cup 32 has an enlarged upper portion which has the same interior diameter as the upper portion 20 of the extraction cartridge such that it may accommodate the same cap 10 if desired. Similarly, the lower portion 34 of the first container 32 is tapered inwardly towards the lower end so that it too may be nested or stacked with a fourth piece of the nested separating apparatus, namely, a second container or cup 36. The first container 32 also forms an exterior shoulder 38 to facilitate its mounting in a holder such as the swinging bucket of a centrifuge. A similar shoulder 40 is formed on the second cup 36 between the lower portion 42 of the container 32 and an enlarged upper portion 44. This enlarged upper portion 44 has an interior diameter which is substantially the same as those of the enlarged portions of the extraction cartridge and the first container. In this manner the cap 10 may be used interchangeably with either of these three units.

The bottom of both the first container 32 and the second container 36 are formed with an annular flange or ring 49 which provides a suitable stand or support for holding both the waste container and the recovery cup in an upright position when placed upon a horizontal surface. Similarly, the bottom wall 46 of the first container and the bottom wall 48 of the second may be slightly cupped such that small quantities of sample material will collect in the center and thereby be more easily concentrated.

The interior of the lower portion of the first container 32 is formed with inwardly projecting radial guides or flanges 29 which are adapted to accommodate and support the nozzle 28 and prevent its being otherwise damaged. The flanges 29 are illustrated as being weblike although other configurations may be used as well. It is important that the nozzle not be damaged so as to not disturb its use in fluid switching as is described in said copending application.

Various materials may be used for the separating column. These are for the most part known, but by way of example, include the ion exchange resins which may be used for the sorption of organic and inorganic ions typically for trace impurity removal, i.e., aminoacid, sugar, protein and peptide analysis. These ion exchange resins include anion, cation and mixed bed. A preferred resin, although not an ion exchange resin, is a cross-linked styrene-divinylbenzene copolymer sold commercially under the tradename "Amberlite" designated XAD-2.

Other column materials that may also be used are gel permeation, which include porous polyacrylamide beads, activated charcoal, agarose gel beads and polystyrene beads. These columns are used for the resolution of compounds of differing molecular weights. Another column material is that used for affinity chromatography and includes agarose supports, polyacrylamide supports and polystyrene supports to which a specific compound has been bonded. Other columns for specific separations are well known in the art and need not be mentioned here.

Suffice it to say, that whatever the column material selected, it should be particulate and sized appropriately to essentially prevent fluid flow therethrough under normal (one X) gravity conditions and yet to accommodate the desired radial fluid flow when more than one X gravity such as provided by centrifugal force that is applied to the column. One particular size that has been used successfully in this regard is particles of the "Amberlite" XAD-2 resin sized in the 40 to 100 micron range with the centrifuge spun at 1000 rpm with the columns located at an average radial distance of 11 cm from the spin axis. Other resins and materials may require different sizing. Alternatively, the porous frits may be sized to achieve these same flow restrictions.

Some extraction cartridges may contain a filter in the reservoir for the purpose of trapping solid, particulate or fibrous materials that may be present in the sample, i.e., fibrin in plasma samples, or amorphous materials in urine samples. The filter protects the porous plug and the column. The filter may be loose and porous such as glass wool, cotton, polyester fiber, or may be solid particles such as glass beads, or even nylon and the like. Glass beads are preferred.

Following the sample recovery, the cap 10 may be placed on top of the recovery cup 36 and the sample retained until it is desired to analyze it either by gas chromatography, liquid chromatography or other appropriate analytical technique.

If desired, a pump (suction or pressure) may be used to move the fluid through the column. For this purpose a pump pressure should provide hydraulic pressure of more than ¼ bar. Compressed gas may be used as the driving force. In either case, the finer column particles permit a more effective separation at the higher fluid flow rates afforded.

The apparatus of this invention is thus seen to be a highly useful column comprising a four-element stacked array which facilitates the labeling of the four compartments while they are together. This reduces sample mix-up. Further, in a simple form, any evaporation from the column is prevented such that the column is in a ready-to-use condition when placed in a centrifuge or other device. All of the elements are readily supported by their respective shoulders in the swinging bucket of the centrifuge or other holder.

We claim:

1. Apparatus for processing fluids comprising, in combination,
    an extraction cartridge having an enlarged middle portion, tapered inward toward its lower end, adapted to receive said fluids and a tubular lower portion communicating with said middle portion,
    separating column material disposed in said lower portion, the bottom end of said lower portion defining a nozzle for fluids passing through said lower portion,
    a first container, the interior lower end of said container defining longitudinal interiorly extending radial guides for positioning said lower portion of said extraction cartridge and protecting said nozzle,
    the top portion of each of said extraction cartridge and said first container defining enlarged sections of equal inside diameter,
    a closure member insertable into the top end of either said extraction cartridge or said first container,
    said extraction cartridge middle portion and said first container each formed to have a mating taper to permit the nesting and sealing of said cartridge in said container, whereby said separating column material and said nozzle are protected and sealed when said closure member is inserted in said cartridge and said cartridge is nested in said first container.

2. The apparatus of claim 1 wherein said separating column material contains particles sized to essentially inhibit a fluid flow under the influence of a centrifugal force of one X gravity, but which permits controlled flow to effect extraction of constituents of said fluid under the influence of a centrifugal force greater than one X gravity.

3. The apparatus of claim 2 which also includes a second container formed to have a mating taper with said first container to permit the nesting of said first container in said second container.

4. The apparatus of claim 3 wherein a porous sphere is positioned at either end of said separating column material for retention thereof in said lower portion.

5. The apparatus of claim 4 wherein said separating column material is an ion exchange resin.

6. The apparatus of claim 5 wherein the top portion of said container defines an enlarged section having an inside diameter equal to the inside diameter of said first container, said enlarged sections define respective exterior step portions which are useable for suspending said cartridge and said containers for centrifugation.

7. The apparatus of claim 1 wherein said enlarged sections define respective exterior step portions which are useable for suspending said cartridge and said container for centrifugation.

8. The apparatus of claim 1 which also includes a second container formed to have a mating taper with said first container to permit the nesting of said first container in said second container.

9. The apparatus of claim 1 wherein the lower portion of said cartridge includes means to essentially inhibit a fluid flow under the influence of a centrifugal force of one X gravity, but which permits controlled flow to effect extraction of constituents of said fluid under the influence of a centrifugal force greater than one X gravity.

10. The apparatus of claim 1 wherein said separating column material contains particles sized to essentially inhibit fluid flow unless under the influence of a head of more than ¼ bar.

11. The apparatus of claim 1 wherein said separating column contains means to essentially inhibit fluid flow unless under the influence of a head of more than ¼ bar.

12. The apparatus of claim 1 wherein a filtration medium is disposed in said extraction cartridge above said column material.

* * * * *